(12) United States Patent
Nakanishi

(10) Patent No.: US 6,558,667 B2
(45) Date of Patent: May 6, 2003

(54) METHOD FOR TREATING RENAL DISEASE, AND PHARMACEUTICAL COMPOSITION FOR TREATING RENAL DISEASE

(75) Inventor: Tsutomu Nakanishi, Kanagawa (JP)

(73) Assignee: Kureha Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 09/840,024

(22) Filed: Apr. 24, 2001

(65) Prior Publication Data

US 2002/0155165 A1 Oct. 24, 2002

(51) Int. Cl.$^7$ .................. A01N 25/00; A01N 37/00; A61K 31/715; A61K 31/52; A61K 45/00

(52) U.S. Cl. .................. 424/126; 514/557; 514/54; 514/263; 424/85.1; 424/600

(58) Field of Search ................. 424/125, 85.1; 514/557, 54, 263

(56) References Cited

U.S. PATENT DOCUMENTS 4,681,764 A * 7/1987 Endo et al.
6,156,797 A * 12/2000 Kubo et al. ............. 514/557

OTHER PUBLICATIONS

Koide et al. "A study of oral adsorbent in chronic renal failure", Biomaterials, Art. Cells & Immo. Biotech. (1991).*

Abstract—P–224, Maintenance of Residual Renal Function by Early Introduction of a CAPD and Effects of Oral Adsorbent Thereon (Ohta Polyclinic Hospital, Toho University, Department of Nephrology The 43$^{rd}$ Annual Meeting Japanese Society of Nephrology, vol. 42 No. 3 (73–326), 2000.

* cited by examiner

Primary Examiner—Jose G. Dees
Assistant Examiner—Robert M DeWitty
(74) Attorney, Agent, or Firm—Sughrue Mion, PLLC

(57) ABSTRACT

A method for treating a patient suffering from a renal failure progressed to a stage at which an initiation of a dialysis therapy is required, comprising combining a peritoneal dialysis and an administration of a spherical carbon, is disclosed.

8 Claims, No Drawings

METHOD FOR TREATING RENAL DISEASE, AND PHARMACEUTICAL COMPOSITION FOR TREATING RENAL DISEASE

BACKGROUND OF THE INVENTION

1. Field of the Invention

The present invention relates to a method for treating a renal disease, and a pharmaceutical composition for treating a renal disease. More particularly, a method for ameliorating a chronic renal failure by a combination of a dialysis therapy and a spherical activated carbon administration, and a pharmaceutical composition for treating a chronic renal failure by a combination of a dialysis therapy and a spherical activated carbon administration.

2. Description of the Related Art

A normal kidney excretes waste materials, regulates an amount of humors (water content), provides an electrolyte balance, an acid-base equilibrium, and blood pressure, and produces hormones. A condition wherein the kidney is prevented from functioning normally, as above, and thus a homeostasis is not maintained, is called a renal failure. An acute renal failure is curable, whereas a chronic renal failure is an irreversible and progressively pathologic state. When a patient suffers a chronic renal failure, the renal functions are not recovered, and he or she will inevitably suffer from uremia. It is believed that it is impossible to heal or recover a chronic renal failure, but only to delay a worsening rate, or retard a presence of symptoms of uremia.

The functions of a kidney can be evaluated by one of several indexes, i.e., an excreting function, which is one of the most important functions. The index of the excreting function is, usually, an endogenous creatinine clearance (Ccr) that corresponds nearly to an amount of a glomerular filtration. Ccr indicates a renal excreting function for a creatinine that is a metabolite of a muscle, and can be regarded as a representative or standard value of the excreting function of a kidney. A normal value of Ccr is 70 to 130 mL/min.

A urine volume is also used as one of the parameters reflecting renal functions, because it generally is decreased with a decrease of renal functions (except for cases wherein a urine volume is temporarily increased when an abnormality in a filtrating function of a kidney is caused), and in particular, is remarkably decreased in an end-stage renal failure. A normal value of a urine volume is 1000 to 1500 mL/day.

The Ccr decreases with a progress of a chronic renal dysfunction, such as chronic glomerulonephritis, diabetic nephropathy, or nephrosclerosis. In general, a state having a Ccr value of 30 mL/min or less is called a chronic renal failure. After a pathologic state reaches such a chronic renal failure, a renal function, i.e., a residual renal function, cannot be recovered, and ultimately the pathologic state reaches a state of uremia. A serious state having a decreased Ccr value of 10 mL/min or less is called uremia. After a pathologic state reaches uremia, a urine volume falls generally to 1000 mL/day or less. As above, in a pathologic state of a chronic renal failure, the Ccr and the urine volume gradually decrease with a deterioration of a residual renal function, and when the pathologic state is worsened, the Ccr and the urine volume cannot be recovered.

A patient having an insufficient function of excretion with a progress of a chronic renal failure is introduced to a dialysis therapy. The stage at which the dialysis therapy is introduced varies with a condition of a patient, but in general, the dialysis therapy is introduced when a Ccr value becomes 10 mL/min or less or a creatinine value becomes 8 mg/dL or more. The dialysis therapy is carried out for an end-stage patient having a progressive chronic renal failure, to remove urine toxins, water, or salt, adjust an acid-base balance inclining to a metabolic acidosis, and maintain homeostasis in a body. The dialysis therapy is classified broadly into two major classes, that is, a hemodialysis (HD) and a peritoneal dialysis (PD).

In the hemodialysis, blood is brought into contact with a dialysis solution via a semipermeable membrane such as a cellophane membrane installed in an extracorporeal dialyzer. The hemodialysis must be carried out in a hospital or the like where the dialyzer is located. Therefore, the patient must periodically and frequently visit a hospital, and thus a quality of life, QOL, is considerably impaired.

In the peritoneal dialysis, on the other hand, a peritoneum in a patient's body is used as a dialysis membrane. More particularly, the peritoneum is composed of a peritoneum parietale covering an abdominal wall and a peritoneum viscerale covering various internal organs, and functions as a semipermeable membrane, and thus can be utilized as a dialysis membrane. The peritoneal dialysis does not require frequent visits to a hospital, and is preferable in comparison with the hemodialysis in view of the QOL.

However, it is known that the introduction of the hemodialysis or peritoneal dialysis leads to a rapid deterioration of a residual renal function. It is said that the residual renal function can be generally maintained for a long period of time by the peritoneal dialysis, in comparison with the hemodialysis. However, for example, Nephrol Dial. Transplant, (1999) 14: 1224–1228 discloses that a renal function was decreased by 57% in a patient treated by an automated peritoneal dialysis (APD), and by 24% in a patient treated by a continuous ambulatory peritoneal dialysis (CAPD).

Therefore, there arose an urgent need for a means of retarding a deterioration of a residual renal function in a patient suffering from a chronic renal failure and to whom a dialysis therapy is introduced.

An oral adsorbent that can be orally administered, and enables a treat of a dysfunction of a kidney is known. Specifically, U.S. Pat. No. 4,681,764 discloses an adsorbent composed of a porous spherical carbonaceous material having specific functional groups, having a high level of safety for and stability in a body, exhibiting a useful selective adsorbability, that is, exhibiting an excellent adsorbability of toxic substances in the presence of intestinal bile acids while removing very little of the internal useful ingredients such as digesting enzymes, and having little side effects such as constipation. The adsorbent is widely and clinically used for a renal dysfunction patient having more than a certain level of a renal function, i.e., a patient in a conserving stage prior to an introduction of a dialysis therapy.

Attempts to combine the oral adsorbent and the dialysis therapy are reported. For example, two clinical cases are reported in S. Takara, et al. "Jin-To-Toseki (Kidney and Dialysis)" Vol. 20, No. 6,1986, 81–85. In the first case, an oral adsorbent was administered to a patient in a conserving stage. When the patient's conditions became worse, the oral adsorbent was discontinued, and a peritoneal dialysis was instituted under conditions of a blood urea nitrogen (BUN) of 120 mg/dL, a creatinine value (Cr value) of 13.2 mg/dL, and a urine volume of 1500 mL/day. Further, when the patient's conditions became severe, a hemodialysis was introduced and an administration of the oral adsorbent at a urine volume of 300 to 200 mL/day was made while continuing the peritoneal dialysis. In the second case, the oral adsorbent was administered to a patient in a conserving stage. A hemodialysis was introduced to the patient under conditions of a BUN of 140 mg/dL and a Cr value of 7.8 mg/dL while increasing a dose of the oral adsorbent. Then, the hemodialysis was substituted with a peritoneal dialysis under the condition of a urine volume of 100 mL/day. Takara, et al., disclose that clinical symptoms were ameliorated in each case. However, clinical data disclosed in Takara, et al., show that, when a combination of the peritoneal dialysis and the oral adsorbent was started, the urine volume was decreased to 300 to 200 mL/day (the first case) and to 100 mL/day (the second case), and then, in the first case, the urine volume was decreased to 0 mL/day after about 10 months from the beginning of the combination of the peritoneal dialysis and the oral adsorbent, and the hemodialysis, and in the second case, the urine volume was decreased to 0 mL/day after about 8 months from the beginning of the combination of the peritoneal dialysis and the oral adsorbent. It is apparent that the residual renal function became worse in each case. As above, Takara, et al., show that the combination of the peritoneal dialysis and the oral adsorbent brings about a clinical improvement, but do not teach a maintenance or an improvement of a residual renal function. It is believed, taking into account the findings of the present inventor as mentioned below, that the combination of the peritoneal dialysis and the oral adsorbent was begun too late.

N. Kawamura, et al., disclose in "Nippon-Tosekiryoho-Gakkai-Shi (Journal of Japanese Society of Dialysis Therapy)", 26(S-1), 1993, 854 that a long-term CAPD patient poses a problem of insufficient dialysis due to a deterioration of a peritoneum function. Further, they disclose a clinical case wherein a patient succeeded in leaving a hemodialysis by beginning an administration of the oral adsorbent to the patient to whom the hemodialysis was introduced, in addition to a peritoneal dialysis, because a dialysis only by a peritoneal dialysis was insufficient due to a deterioration of a peritoneum function; and another case wherein an administration of the oral adsorbent was successful to some extent in the case of uremic symptoms due to an insufficient dialysis only by a peritoneal dialysis. However, Kawamura, et al., merely disclose an effect of the oral adsorbent as an auxiliary means for preventing an insufficient dialysis only by a peritoneal dialysis, but do not teach a maintenance or an improvement of a residual renal function.

Some studies have indicated that an early introduction of the peritoneal dialysis lowers a mortality rate in comparison with a later introduction thereof. However, there are only a few reports describing a relationship between the early introduction of the peritoneal dialysis and the residual renal function, and thus, the effect of the early introduction has not yet been clearly defined. Further, it has not been expected at all that the early introduction of the peritoneal dialysis can recover the residual renal function.

SUMMARY OF THE INVENTION

The present inventor carried out investigations into a means of recovering a residual renal function of a patient affected with a chronic renal failure progressed to a stage at which a dialysis therapy should be initiated, and of leaving the dialysis therapy. As a result, the present inventor found that a residual renal function can be improved or recovered, or as the case may be, a patient can be taken off a peritoneal dialysis, by beginning the peritoneal dialysis at a stage at which a sufficient urine volume and a residual renal function are maintained, and administering the oral adsorbent at the same time. The above finding is surprising from the conventional commonsense standpoint that an improvement or recovery of a renal function in a patient affected with a chronic renal failure is impossible.

The present invention is based on the above findings.

An object of the present invention is to provide a means of recovering a renal function of a patient affected with a chronic renal failure progressed to a stage at which an initiation of a dialysis therapy is required, and a means capable allowing a leaving of the dialysis therapy if a good recovery is made. Other objects and advantages will be clear from the following description.

Accordingly, the present invention relates to a method of treating a patient suffering from a renal failure, particularly, a chronic renal failure, progressed to a stage at which an initiation of a dialysis therapy is required, comprising combining a peritoneal dialysis and an administration of a spherical carbon.

Further, the present invention relates to a pharmaceutical composition for treating a patient suffering from a renal failure, particularly, a chronic renal failure, progressed to a stage at which an initiation of a dialysis therapy is required, comprising an effective amount of a spherical carbon and a pharmaceutically acceptable carrier or diluent to be administered to the patient together with an initiation of a peritoneal dialysis.

DESCRIPTION OF THE PREFERRED EMBODIMENTS

The expression "a patient suffering from a renal failure progressed to a stage at which an initiation of a dialysis therapy is required" as used herein means a patient affected with a renal failure at a stage close to criteria for an initiation of a dialysis therapy, or an early stage after reaching criteria for an initiation of a dialysis therapy. Specifically, the "patient suffering from a renal failure progressed to a stage at which an initiation of a dialysis therapy is required" means a patient under conditions such that a certain level of a urine volume is maintained, a creatinine clearance is decreased to a certain level or more, due to a deterioration of a renal function, clinical symptoms, such as a stagnation of humor or gastrointestinal symptoms, emerge, and troubles are encountered in daily life; a patient who cannot prevent uremic symptoms due to a renal failure from emerging without an introduction of a dialysis therapy, in particular, a patient suffering from a chronic renal failure.

To the best of the inventor's knowledge, it is not known in the prior art to carry out a combined therapy of a peritoneal dialysis and a spherical carbon administration at an early stage after reaching criteria for an initiation of a dialysis therapy wherein a certain level of a urine volume is maintained. Further, it is not known at all in the prior art that a renal function can be recovered, or in some cases, a patient can be taken off a peritoneal dialysis, by carrying out the combined therapy of the peritoneal dialysis and the spherical carbon administration at an early dialyzing stage.

Therefore, the "patient suffering from a renal failure progressed to a stage at which an initiation of a dialysis therapy is required" means, for example, a patient affected with a renal failure and having a urine volume of, preferably 800 mL/day or more, more preferably 1000 mL/day or more, most preferably 1500 mL/day or more.

The "patient suffering from a renal failure progressed to a stage at which an initiation of a dialysis therapy is required" means, for example, a patient affected with a renal failure and having a creatinine clearance (Ccr) of, preferably 5 mL/min or more, more preferably 8 mL/min to 30 mL/min, most preferably 10 mL/min to 25 mL/min.

Further, the "patient suffering from a renal failure progressed to a stage at which an initiation of a dialysis therapy is required" means, for example, a patient affected with a renal failure and having a BUN of, preferably 40 mg/dL to 150 mg/dL, more preferably 40 mg/dL to 100 mg/dL.

Furthermore, the "patient suffering from a renal failure progressed to a stage at which an initiation of a dialysis therapy is required" means, for example, a patient affected with a renal failure and having a serum creatinine (s-Cr) of, preferably 3 mg/dL to 10 mg/dL, more preferably 4 mg/dL to 8 mg/dL.

Still further, the "patient suffering from a renal failure progressed to a stage at which an initiation of a dialysis therapy is required" means, for example, a patient not having been treated by a dialysis therapy.

In the present invention, any known peritoneal dialysis can be utilized. The peritoneal dialysis which may be used in the present invention is, for example, a continuous ambulatory peritoneal dialysis (CAPD), an intermittent peritoneal dialysis (IPD), or an automated peritoneal dialysis (APD), such as a continuous cyclic peritoneal dialysis CCPD), or a nightly peritoneal dialysis (NPD). In the present invention, the above-mentioned peritoneal dialysis may be used alone or in a combination thereof. In the present invention, it is unnecessary to carry out, but preferable not to carry out, a hemodialysis in addition to the peritoneal dialysis.

A dialysis solution used in the peritoneal dialysis according to the present invention may be a conventional dialysis solution usually used in a conventional peritoneal dialysis.

In the present invention, a spherical carbon is administered in combination with the peritoneal dialysis.

The spherical carbon used in the present invention is not particularly limited as long as the spherical carbon has a spherical shape that can be used for medical treatment. A medical powdery activated carbon conventionally used as an antidote has the side effect of easily causing constipation. Constipation during an illness is particularly dangerous, and thus the above point is a major defect.

The spherical carbon used in the present invention has a particle diameter of 0.05 to 2 mm. When the particle diameter is less than 0.05 mm, the function for eliminating toxic substances becomes insufficient, but a side effect, such as constipation, easily occurs. When the particle diameter is over 2 mm, not only does administration become difficult, but also the desired pharmacological effect is not quickly obtained. The shape of the spherical carbon is one of the important factors for obtaining the effect of the present invention, and it must be substantially spherical.

In the production of the spherical carbon used in the present invention, any raw material from which activated carbon is obtained may be used, for example, sawdust, coal, coconut shells, petroleum pitches, coal pitches, or synthetic organic polymers. It is preferable to use petroleum hydrocarbons. In the present invention, it is preferable to use activated spherical carbon and/or spherical adsorbent (i.e., spherical carbonaceous adsorbent), more preferably the spherical adsorbent, as the spherical carbon.

The activated spherical carbon that may be used in the present invention has a diameter of 0.05 to 2 mm. The basic method for the production of activated spherical carbon comprises carbonizing a starting material and then activating the carbonized material. As the method used for the activation, it is possible to use various known methods for an activation by, for example, steam, chemicals, air, and carbon dioxide. The activated spherical carbon can be prepared, for example, by the following three methods.

A first method comprises the steps of forming fine spherical particles by pelletizing a powdery material with a binder such as pitch; carbonizing the particles by baking in an inert atmosphere at 600 to 1000° C.; and then activating the carbonized particles in a steam atmosphere at 850 to 1000° C.

A second method comprises, as disclosed in, for example, U.S. Pat. No. 3,917,806, corresponding to Japanese Examined Patent Publication (Kokoku) No. 51-76, forming molten pitch into fine spherical particles; rendering the particles infusible by oxygen; and then carbonizing and activating the infusible particles in the same manner as in the first method.

A third method comprises, as disclosed, for example, in U.S. Pat. No. 4,420,443, corresponding to Japanese Examined Patent Publication (Kokoku) No. 59-10930, forming string-like pitch in a molten state; crushing the string-like pitch; introducing the crushed pitch into hot water to form spherical particles; rendering the particles infusible by oxygen; and then carbonizing and activating the infusible particles in the same manner as in the first method.

The spherical carbonaceous adsorbent which may be used in the present invention preferably has the following parameters: a particle diameter of 0.05 to 2 mm, an amount of pores having a radius of not more than 80 Angstroms accounts for 0.2 to 1.0 mL/g, a total amount of acidic groups (A) of 0.30 to 1.20 meq/g, a total amount of basic groups (B) of 0.20 to 0.70 meq/g, and a ratio of the total amount of acidic groups (A) to the total amount of basic groups (B) of 0.40 to 2.5. The spherical carbonaceous adsorbent is disclosed in, for example, U.S. Pat. No. 4,681,764.

It is possible to prepare the spherical carbonaceous adsorbent which may be used in the present invention, by further oxidizing and reducing at an elevated temperature the activated spherical carbon having a particle diameter of 0.05 to 2 mm and a pore amount of 0.2 to 1.0 mL/g for pores having a radius of not more than 80 Angstroms. It is preferable to adjust, by the above oxidizing and reducing treatment at an elevated temperature, the acidic and basic groups of the resulting spherical carbonaceous adsorbent; namely, a total amount of acidic groups (A) to 0.30 to 1.20 meq/g, a total amount of basic groups (B) to 0.20 to 0.70 meq/g, and a ratio of the total amount of acidic groups (A) to the total amount of basic groups (B) to 0.40 to 2.5. The total amount of acidic groups (A) and the total amount of basic groups (B) are physical properties determined by ordinary methods, as follows:

(A) Total Amount of Acidic Groups (A)

The amount of NaOH consumed, which may be determined by adding 1 g of activated spherical carbon or spherical carbonaceous adsorbent, after being crushed into particles having a less than 200 mesh size, to 50 mL of a 0.05N NaOH solution; shaking the mixture for 48 hours; then filtering out the activated spherical carbon or spherical carbonaceous adsorbent; and titrating until neutralization.

(B) Total Amount of Basic Groups (B)

The amount of HCl consumed, which may be determined by adding 1 g of activated spherical carbon or spherical carbonaceous adsorbent after being crushed into particles having a less than 200 mesh size, to 50 mL of a 0.05N HCl solution; shaking the mixture for 24 hours; then filtering out the activated spherical carbon or spherical carbonaceous adsorbent; and titrating until neutralization.

The above oxidizing treatment at an elevated temperature is carried out by a heating treatment at an elevated temperature in an oxidizing atmosphere. As the source of oxygen, pure oxygen, nitrogen oxide, air, or the like may be used. Further, the above reducing treatment at an elevated temperature is carried out by a heating treatment at an elevated temperature in an atmosphere inert to carbon. As the inert atmosphere for the carbon, nitrogen, argon, helium, or mixtures thereof may be used. The conditions of the above heating-oxidation treatment are an atmosphere containing preferably 0.5 to 25% by volume of oxygen, more preferably 3 to 10% by volume of oxygen, and a temperature of preferably 300 to 700° C., more preferably 400 to 600° C. The reduction treatment is preferably carried out in a nitrogen atmosphere at a temperature of 700 to 1100° C., more preferably 800 to 1000° C.

In the present invention, the spherical carbon is administered orally. The dosage thereof depends on the subject (animal or human), age, individual differences, disease conditions, and so on. For example, the oral dosage in the case of a human is usually 0.2 to 20 g of spherical carbon per day. The daily dosage may be taken up at one time or divided into two to four portions. The dosage may appropriately vary with the disease conditions. The spherical carbon formulation may be administered in any form such as granules, tablets, sugar-coated tablets, capsules, sachets, divided packages, suspensions, or the like. In the case of capsules, the usual gelatin capsules, or if necessary, enteric capsules may be used. In the case of granules, tablets, or sugarcoated tablets, these formulations must be broken into the original fine particles inside the body.

The present invention encompasses the case wherein the spherical carbon is administered to a patient affected with a renal failure but not experiencing a dialysis therapy, and after the conditions of the patient progresses to a stage at which an initiation of a dialysis therapy is required, then a peritoneal dialysis is introduced to the patient while continuing the administration of the spherical carbon. Further, the present invention encompasses the case wherein a peritoneal dialysis is introduced and at the same time an administration of the spherical carbon is commenced to a patient affected with a renal failure but not experiencing a dialysis therapy, but not taking the spherical carbon, after the conditions of the patient progresses to a stage at which an initiation of a dialysis therapy is required.

According to the present invention, a renal function is recovered by a combined treatment of the peritoneal dialysis and the spherical carbon administration at a specific stage. Further, if a good recovery is obtained, the peritoneal dialysis can be suspended, or a patient can be taken off the peritoneal dialysis, as shown in Example 1 as mentioned below.

EXAMPLES

The present invention now will be further illustrated by, but is by no means limited to, the following Examples.

Preparation Example 1

Preparation of Spherical Carbonaceous Adsorbent

Pitch (300 g) (ratio of hydrogen atoms/carbon atoms= 0.55; flowing point=220° C.) having an anisotropic region that was not localized under a polarization microscope and naphthalene (100 g) were charged into an autoclave equipped with a stirrer, melted at 180° C., and mixed. Then, 1200 g of a 0.5% polyvinyl alcohol aqueous solution was added. The mixture was further vigorously stirred at 140° C. for 30 minutes and cooled to room temperature under stirring to obtain spherical particles. After a large part of the water was filtered out, the resulting spherical particles were charged into an extractor. Hexane was passed through the particles to extract and remove the naphthalene, and the particles were dried with air. Thereafter, the particles were heated on a fluid bed with heated air passed therethrough by raising the temperature to 300° C. at a rate of 25° C./h, and were further maintained at 300° C. for 2 hours to render them infusible. Then, the infusible particles were heated by raising the temperature to 900° C. in steam and kept at 900° C. for 2 hours in steam to be carbonized and activated, whereby porous activated spherical carbon was obtained. The diameter of the resulting activated spherical carbon was 0.05 to 1.0 mm and an amount of pores having a radius of not more than 80 Angstroms was 0.755 mL/g (determined by a methanol adsorption method using an automatic adsorption measuring apparatus).

The resulting activated spherical carbon particles were then treated for 3 hours at 600° C. in an atmosphere of a 3% oxygen on a fluid bed, then heated to 950° C. in a nitrogen atmosphere and kept at 950° C. for 30 minutes to obtain the spherical carbonaceous adsorbent. The diameter of the resulting spherical carbonaceous adsorbent was 0.05 to 1 mm, the amount of pores having a radius of not more than 80 Angstroms was 0.751 mL/g (according to the methanol adsorption method using an automatic adsorption measuring apparatus), the total amount of acidic groups (A) was 0.542 meq/g, the total amount of basic groups (B) was 0.525 meq/g, and the ratio of the total amount of acidic groups (A)/total amount of basic groups (B) was 1.03.

In an acute toxicity test made by orally administering the spherical carbonaceous adsorbent to rats (Cpb; WU; Wistar Random), no abnormalities were observed even with the maximum dosage (5000 mg/kg for male and female rats) according to the Guidelines for Toxicity Studies of Drugs (Notification No. 118 of the Pharmaceutical Affairs Bureau, Ministry of Health and Welfare, Japanese Government, Feb. 15, 1984).

Example 1

As a male patient (age=34) affected with a chronic glomerulonephritis took a sudden turn for the worse, an emergency hemodialysis (HD) was introduced. Thereafter, the condition of the patient improved slightly. However, one month after the emergency hemodialysis, the BUN and s-Cr were increased, and thus, a peritoneal dialysis (PD) was introduced, and at the same time, an administration of the spherical adsorbent prepared in Preparation Example 1 was started at a dose of 6 g/day, to observe the course of the patient. When the combined treatment of the PD and the spherical adsorbent administration was started, the blood urea nitrogen (BUN) was 45 mg/dL, the serum creatinine (s-Cr) was 4.4 mg/dL, the creatinine clearance (Ccr) was 11.4 mL/min, and the urine volume was 3000 mL/day.

The PD used was a nightly peritoneal dialysis (NPD) wherein a treating time was 8 hours, an amount of a dialysis solution charged once was 1.5 to 2.5 L, and three cycles were carried out. The dialysis solution was Dianeal PD-4, i.e., a Ca-low concentration dialysis solution containing 2.5 meq/L calcium and 1.5% glucose.

After the combined treatment of the PDs and the spherical adsorbent administration was started, the NPDs using 1.5% Dianeal PD-4 (2L×3) were continued, and it was found that the amounts of water taken, urine volumes, dialysis solutions charged, and dialysis solutions recovered were well balanced, and the BUN was 20 mg/dL, the s-Cr was 3.2 mg/dL, and the urine volume was 2800 mL/day. These parameters indicated that a residual renal function was maintained.

Further, the combined treatment of the NPDs using 1.5% Dianeal PD-4 (2L×3) and the spherical adsorbent administration was continued. After 2 months from the beginning of the combined treatment, the BUN was 22.2 mg/dL, the s-Cr was 3.4 mg/dL, the urine volume was 2900 mL/day, the residual renal Ccr was 18.0 mL/min, the weekly Kt/V was 3.49, the normalized Ccr was 175 L/week/1.73 m², and the normalized protein catabolic rate (nPCR) was 0.67 g/kg/day.

After 5 months from the beginning of the combined treatment, the BUN and s-Cr showed a tendency to decrease, and thus, the number of times of the use of NPDs was gradually reduced. After 2 months therefrom, the NPD was terminated, but was replaced by a daytime charging of the dialysis solutions while continuing the spherical adsorbent administration under the same dosage. The number of times of use of the daytime charging was gradually reduced. Then, a dietary treatment limiting an amount of proteins taken-up to 0.5 g/kg/day brought about the conditions wherein the BUN was 20 mg/dL, the s-Cr was 3.2 mg/dL, the urine volume was 3000 mL/day, and the Ccr was 25.6 mL/min. The above conditions did not indicate that the condition of the patient became worse, and therefore, the PD was completely terminated. After 2 months from the termination of the PD, the BUN was 19.0 mg/dL, the s-Cr was 2.8 mg/dL, and the Ccr was 24.4 mL/min. These conditions indicated that the patient remained stable.

Example 2

The spherical adsorbent prepared in Preparation Example 1 was administered at a dose of 6 g/day to a male patient (age=50) affected with a renal failure seemingly due to a diabetic nephropathy, for 3 months. Then, a peritoneal dialysis (PD) was introduced while the spherical adsorbent administration was continued. When the combined treatment of the PD and the spherical adsorbent administration was started, the blood urea nitrogen(BUN) was 79 mg/dL, the serum creatinine (s-Cr) was 9.4 mg/dL, the creatinine clearance (Ccr) was 5.1 mL/min, and the urine volume was 1400 mL/day.

As in Example 1, the PD used was a nightly peritoneal dialysis (NPD) wherein a treating time was 8 hours, an amount of a dialysis solution charged once was 1.5 to 2.5 L, and three cycles were carried out. The dialysis solution was Dianeal PD-4, i.e., a Ca-low concentration dialysis solution containing 2.5 meq/L calcium and 1.5% glucose.

After the combined treatment of the PDs and the spherical adsorbent administration was started, the NPDs using 1.5% Dianeal PD-4 (2L×3) were continued, and it was found that the amounts of water taken, urine volumes, dialysis solutions charged, and dialysis solutions recovered were well balanced, and the BUN was 32 mg/dL, the s-Cr was 7.0 mg/dL, and the urine volume was 1800 mL/day. These parameters indicated that a residual renal function was maintained.

Further, the combined treatment of the NPDs using 1.5% Dianeal PD-4 (2L×3) and the spherical adsorbent administration was continued. After 6 months from the beginning of the combined treatment, the BUN was 39 mg/dL, the s-Cr was 5.8 mg/dL, the urine volume was 1600 mL/day, the residual renal Ccr was 5.0 mL/min, the weekly Kt/V was 2.28, the normalized Ccr was 85 L/week/1.73 m², and the normalized protein catabolic rate (nPCR) was 0.83 g/kg/day.

Still further, the combined treatment of the NPDs using 1.5% Dianeal PD-4 (2L×3) and the spherical adsorbent administration was continued. After 16 months from the beginning of the combined treatment, the BUN was 33 mg/dL, the s-Cr was 5.9 mg/dL, the urine volume was 1300 mL/day, the residual renal Ccr was 5.2 mL/min, the weekly Kt/V was 1.47, normalized Ccr was 76 L/week/1.73 m², and the normalized protein catabolic rate (nPCR) was 0.54 g/kg/day.

Still further, the combined treatment as above was continued. After 17 months from the beginning of the combined treatment, the BUN was 38.8 mg/dL, the s-Cr was 6.1 mg/dL, the urine volume was 1300 mL/day, the residual renal Ccr was 6.0 mL/min, the weekly Kt/V was 1.59, the normalized Ccr was 85 L/week/1.73 m², and the normalized protein catabolic rate (nPCR) was 0.62 g/kg/day.

As above, it was apparent from, for example, the results of the residual renal Ccrs that a renal function was improved.

Example 3

The spherical adsorbent prepared in Preparation Example 1 was administered at a dose of 6 g/day to a male patient (age=52) affected with a renal failure seemingly due to a chronic glomerulonephritis, for 1 month. Then, a peritoneal dialysis (PD) was introduced while the spherical adsorbent administration was continued. When the combined treatment of the PD and the spherical adsorbent administration was started, the blood urea nitrogen(BUN) was 57 mg/dL, the serum creatinine (s-Cr) was 9.3 mg/dL, the creatinine clearance (Ccr) was 5.3 mL/min, and the urine volume was 1200 mL/day.

As in Example 1, the PD used was a nightly peritoneal dialysis (NPD) wherein a treating time was 8 hours, an amount of a dialysis solution charged once was 1.5 to 2.5 L, and three cycles were carried out. The dialysis solution was Dianeal PD-4, i.e., a Ca-low concentration dialysis solution containing 2.5 meq/L calcium and 1.5% glucose.

After the combined treatment of the PDs and the spherical adsorbent administration was started, the NPDs using 1.5% Dianeal PD-4 (2L×3) were continued, and it was found that the amounts of water taken, urine volumes, infusion of dialysis solution, and drainage of dialysis solution were well balanced, and the BUN was 30 mg/dL, the s-Cr was 5.9 mg/dL, and the urine volume was 1600 mL/day. These parameters indicated that a residual renal function was maintained.

Further, the combined treatment of the NPDs using 1.5% Dianeal PD-4 (2L×3) and the spherical adsorbent administration was continued. After 8 months from the beginning of the combined treatment, the BUN was 46 mg/dL, the s-Cr was 8.4 mg/dL, the urine volume was 2650 mL/day, the residual renal Ccr was 5.7 mL/min, the weekly Kt/V was 2.32, the normalized Ccr was 83 L/week/1.73 m², and the normalized protein catabolic rate (nPCR) was 0.95 g/kg/day.

As above, it was apparent from, for example, the results of the residual renal Ccrs and urine volumes, that a renal function was improved.

Methods for Determining the Parameters

The parameters as mentioned in the above-mentioned Examples 1 to 3 were measured or calculated as follows:
(1) Creatinine Clearance (Ccr)

A value of the creatinine clearance (Ccr) can be calculated from a following equation:

$$Ccr\ (mL/min) = Ud \times (UCr/BCr)$$

wherein Ud (mL/min) is a urine volume per minute calculated by a daily urine volume, Ucr (mg/dL) is a creatinine concentration in urine, Bcr (mg/dL) is a creatinine concentration in blood.

(2) Serum Creatinine (s-Cr)

A value of the serum creatinine (s-Cr) is determined by a standard blood-biochemical test.

(3) Blood Urea Nitrogen (BUN)

A value of the blood urea nitrogen (BUN) is determined by a standard blood-biochemical test.

(4) Daily Urine Volume

A total volume of urine is measured, after collecting urine excreted over 24 hours.

(5) Residual Renal Ccr

The residual renal Ccr is a creatinine clearance from a kidney of a PD patient, and can be determined by a same method as that disclosed in the above item (1).

(6) Weekly Kt/V

There exists a significant correlation between a value of weekly Kt/Vurea in a hemotherapy and a prognosis for a patient, and therefore, the usefulness of the value is recognized. A value of weekly Kt/Vurea in a PD therapy is calculated by multiplying a total amount of daily drainage by a ratio (D/P) of urea (D) in a dialysis solution to urea (P) in plasma, and dividing the resulting product by a total amount of humor (body weight×0.58). Usually, the resulting value is multiplied by 7 to obtain a value of weekly Kt/v. An optimal value in dialysis that does not cause an insufficient dialysis is 1.7/week.

(7) Normalized Ccr

A value of the normalized Ccr is calculated by correcting Ccr with a surface area (1.48 m$^2$) of a body.

(8) Normalized Protein Catabolic Rate (nPCR)

An amount of proteins taken-up can be estimated by calculating a value of the PCR. The resulting amount of proteins taken-up enables a nutriceutical evaluation of a patient, and thus an efficiency of a dialysis can be indirectly estimated. A value of daily PCR is calculated by multiplying a total amount of nitrogen removed by 6.25. The total amount of nitrogen removed is a sum of urea nitrogen in a drainage, urea nitrogen in urine, nitrogen derived from removed proteins in a drainage (generally 1.39 g/day), nitrogen derived from removed amino acids in a drainage (generally 0.5 g/day), and other nitrogen such as urate or creatinine (generally 0.031 g/day). An average nitrogen content in a protein is 16%, and thus, a daily PCR can be calculated by multiplying the above sum (=a total amount of nitrogen removed) by 6.25 (=1/0.16). A normalized PCR, i.e., nPCR, is a PCR per weight body, and can be calculated by dividing a value of the PCR by a body weight (kg).

(9) Total Creatinine Clearance of a PD Patient

A value of a total creatinine clearance of a PD patient is a sum of a peritoneal creatinine clearance and a residual renal creatinine clearance.

(10) Peritoneal Creatinine Clearance

A value of a peritoneal creatinine clearance (PCcr) can be calculated from a following equation:

$$PCcr = (D/P)cr \times Vpd$$

wherein (D/P)cr is a ratio of (creatinine in a drainage)/(creatinine in blood), and Vpd is a total amount (L) of a drainage. A value of weekly PCcr can be calculated by multiplying PCcr by 7.

Although the present invention has been described with reference to specific embodiments, various changes and modifications obvious to those skilled in the art are deemed to be within the spirit, scope, and concept of the invention.

What I claim is:

1. A method for treating a patient suffering from renal failure progressed to a stage at which initiation of dialysis therapy is required, comprising combining peritoneal dialysis and administration of spherical carbon at a stage at which sufficient urine volume and residual renal function are maintained, wherein the urine volume of said patient is 800 mL/day or more and said patient has a creatinine clearance of 5 mL/min or more.

2. The method according to claim 1, wherein a blood urea nitrogen (BUN) of the patient suffering from a renal failure progressed to a stage at which an initiation of a dialysis therapy is required is 40 mg/dL to 150 mg/dL.

3. The method according to claim 1, wherein a serum creatinine of the patient suffering from a renal failure progressed to a stage at which an initiation of a dialysis therapy is required is 3 mg/dL to 10 mg/dL.

4. The method according to claim 1, wherein the patient suffering from a renal failure progressed to a stage at which an initiation of a dialysis therapy is required is a patient who has not been treated by a dialysis therapy.

5. The method according to claim 1, wherein the spherical carbon is a spherical activated carbon or a spherical adsorbent.

6. The method according to claim 1, wherein the spherical carbon is administered at a dose of 0.2 g/day to 20 g/day.

7. The method according to claim 1, wherein, after a recovery of a renal function by a combined treatment of the peritoneal dialysis and the administration of the spherical carbon is recognized, the peritoneal dialysis is terminated.

8. The method according to claim 1, wherein the spherical carbon is administered to a patient affected with a renal failure but not experiencing a dialysis therapy, and after the condition of the patient progresses to the stage at which an initiation of a dialysis therapy is required, the peritoneal dialysis is introduced to the patient while continuing the administration of the spherical carbon.

* * * * *